United States Patent [19]
Miki et al.

[11] Patent Number: 5,212,095
[45] Date of Patent: May 18, 1993

[54] FLOW INJECTION NONAQUEOUS SOLVENT NEUTRALIZATION TITRATION PROCESS AND APPARATUS

[75] Inventors: Kojiro Miki, Kouga; Shinji Takeichi, Nara; Hiromi Ohkawa, Joyo, all of Japan

[73] Assignee: Horiba, Ltd., Kyoto, Japan

[21] Appl. No.: 854,092

[22] Filed: Mar. 19, 1992

[30] Foreign Application Priority Data

Mar. 22, 1991 [JP] Japan .................................. 3-83086

[51] Int. Cl.$^5$ .................... G01N 35/08; G01N 31/16; G01N 31/22
[52] U.S. Cl. ..................................... 436/52; 436/163; 436/826; 422/68.1
[58] Field of Search ............... 436/163, 52, 826; 422/68.1

[56] References Cited

U.S. PATENT DOCUMENTS

| | | | |
|---|---|---|---|
| 4,269,604 | 5/1981 | Snowden, Jr. ........ | 436/163 |
| 4,654,309 | 3/1987 | Mlinar et al. ........ | 436/61 |
| 5,094,817 | 3/1992 | Aoki et al. ........ | 422/68.1 |
| 5,124,042 | 6/1992 | Bredeweg et al. ........ | 210/651 |

Primary Examiner—James C. Housel
Assistant Examiner—N. Bhat
Attorney, Agent, or Firm—Price, Gess & Ubell

[57] ABSTRACT

A flow injection nonaqueous solvent neutralization titration process and system is provided. The predetermined quantity of a known titrant is used to derived calibration values based on different predetermined concentrations of a desired component in a sample. The quantity of the titrant agent in excess of an amount necessary to completely react with the sample is added and then subsequently the amount of the unreactant titrant agent is determined. From this value, the calibration values that have been stored, for example, in a look-up table can be used to determine the actual concentrations of the desired component in the sample. Alternatively, the sample can be mixed in a fluid carrier solution having a predetermined quantity of the titrant agent and then the resulting by-products of the reaction with the sample and the titrant can be inserted into a pH buffer solution so that the excess titrant will change the concentration ratio of the acids to bases and by measuring this change and comparing with the calibration values, the unknown concentration of the desired component in the sample can be discovered.

7 Claims, 2 Drawing Sheets

FLOW INJECTION NONAQUEOUS SOLVENT NEUTRALIZATION TITRATION PROCESS AND APPARATUS

BACKGROUND OF THE INVENTION

1. Field of the Invention

The present invention relates to a flow injection nonaqueous solvent neutralization titration system used for a quantitative determination of sample lubricants, such as used in an engine, edible oils and fats and other acids and base material.

2. Description of Related Art

In a titrimetric process, the concentration of a substance in a solution is determined in terms of the smallest amount of the reagent of a known concentration required to bring about a given effect and reaction with a known volume of the test solution.

A nonaqueous solvent neutralization titration process has been useful in making a quantitative determination of weak acids and bases, which are insoluble to water or weak in strength as acids and bases in water and thus difficult to be titrated, and has been used for quantitative determination of lubricants, edible oils and fats and other acids and base materials.

As for the nonaqueous solvent neutralization titration, a flow injection nonaqueous solvent neutralization titration apparatus, which is shown schematically in FIG. 5, has been known as an apparatus to quickly titrate acids or bases.

Referring to FIG. 5, reference numeral 11 designates a pH buffer solution line, reference numeral 12 designates a carrier solution line, connected with pH buffer solution line 11 at a confluence point 13. A reaction coil 14 is arranged on the downstream side of the confluence point 13, and a pH-electrode detector 15 is also arranged on the downstream side of the reaction coil 14. Reference numeral 16 designates a pump, provided in the pH buffer solution line 11 and the carrier solution line 12, and reference numeral 17 designates an injector of a sample arranged in the carrier solution line 12.

In a titration method by means of the above flow injection nonaqueous solvent neutralization titration apparatus, the pumps 16 are driven to supply the pH buffer solution line 11 with a pH buffer solution consisting of a nonaqueous solvent having an acid-base buffer capacity and the carrier solution line 12 with ethanol as a carrier solution, respectively, and a sample is set in the injector 17 to inject the sample into the carrier solution. The carrier solution, into which the sample has been injected, is joined with the pH buffer solution at the confluence point 13 and the sample acts upon active ingredients within the pH buffer solution at the reaction coil 14 to change a concentration ratio of acids to bases in the pH buffer solution. This ratio is detected by means of the pH detector 15 to carry out a quantitative determination from a peak-height of the detected signal on the basis of a previously prepared calibration curve (not shown).

Since a stream of the pH buffer solution is utilized in the above described manner in the flow injection nonaqueous solvent neutralization titration, the quantitative determination of acids (or alkalies) can be quickly achieved. However, in this nonaqueous solvent neutralization titration, a slope of the calibration curve between a sample concentration and a peak-height is dependent upon a ratio of a dissociation constant of acids (or alkalies) of the pH buffer solution to that of acids (or alkalies) in the sample, so that a problem can occur in that the quantitative determination cannot be achieved unless the dissociation constant of acids (or alkalies) in the sample is known. Accordingly, it is difficult to apply the above described titration method to the determination of a neutralization value of petroleum products to the above described titration method.

In addition, a back titration method, in which an excess of a titrant is added to the sample to neutralize acids (or alkalies) of the sample and then the concentration ratio of acids to bases of the H buffer solution is changed by the remaining titrant, has been known as a titration method of determining a neutralization value of petroleum products which are mixtures of many kinds of acid (or alkali) but this reverse titration method does not require a preparation of a calibration curve.

In the above described back titration method, an excess of a titrant is added, so that acids (or alkalies) in the sample can be quantitatively determined even though their dislocation constants are unknown. However, since a calibration curve is not used, a problem occurs in that it is required to strictly control the quantity and concentration of the titrant.

Accordingly the prior art is still seeking an efficient and improved titration process and apparatus.

SUMMARY OF THE INVENTION

The present invention solves the above described prior art problems and provides a flow injection nonaqueous solvent neutralization titration process capable of achieving a quantitative determination of a sample without requiring a strict control of the quantity and concentration of a titrant, even though a dissociation constant of acids (or alkalies) in a sample is unknown.

A first embodiment of a flow injection nonaqueous solvent neutralization titration process according to the present invention is characterized in that an excess of titrant for neutralizing acids (or base) materials is added to the sample and then the sample is injected into a stream of a carrier solution to join a stream of the carrier solution with a stream of a pH buffer solution, thereby changing a concentration ratio of acids to bases of the pH buffer solution with the remaining active titrant, followed by detecting a change of the concentration ratio of acids to bases by means of a detector to quantitatively determine the acids or bases in the sample from a peak-height of the detected signal by the use of a separately prepared calibration curve for a known substance.

A second embodiment is characterized in that a sample is injected into a stream of a carrier solution, to which an excess of titrant has been added to neutralize the acids (or bases) in the sample. The sample is introduced into the stream of the carrier solution and is joined downstream with a stream of a pH buffer solution to change a concentration ratio of acids to bases of the pH buffer solution with the remaining titrant followed by detecting any change of the concentration ratio of acids to bases by means of a detector to quantitatively determine the acids or bases in the sample from a peak-height of the detected signal by the use of a separately prepared calibration curve for a known substance.

A nonaqueous solvent pH buffer solution, such as a trichloro acetic acid/n-propyl amine buffer solution, mainly comprising a nonaqueous solvent, is used as the above described pH buffer solution. For example, a solvent (toluene:isopropyl alcohol:water=50:49.5: 0.5) provided in JIS K2501, isopropyl alcohol or the like, can be used as the carrier solution. The titrant to be added to the sample or the carrier solution is, for example, HCl, $H_2SO_4$, and the like.

A pH detector or an absorptivity detector is used as the detector, but a pH indicator is added to the pH buffer solution when the absorptivity detector is used.

In the flow injection nonaqueous solvent neutralization titration according to the first embodiment, an excess of titrant neutralizing acids or bases in a sample is put in a suitable container, such as a beaker. Thereupon, the sample is dispersed in the solvent to neutralize acids or bases in the sample with the titrant, but since an excess of titrant has been added, a portion of a nonreacted titrant remains. The sample, of which acids or bases have been neutralized with the titrant in such a manner, is injected into the carrier solution flowing through a carrier solution line to be joined with the pH buffer solution.

As soon as the stream of the carrier solution is joined with the stream of the pH buffer solution, the above described nonreacted titrant acts upon ingredients in the stream of the pH buffer solution to change the concentration ratio of acids to bases of the pH buffer solution, so that the concentration ratio of acids to bases can be detected by means of a detector to determine a peak-height of the detected signal. The peak-height of the detected signal will be reduced with an increase of a base-number of the sample.

Accordingly, the base-number of the sample is measured from the peak-height of the detected signal obtained with injecting the sample on the basis of a calibration curve between the base-number and the peak-height of the detected signal prepared by injecting different known substances, of which base-numbers have been known. Since the titrant is previously added to the sample to carry out the neutralization reaction in the above described manner, a sample having a large viscosity can be treated.

In the second embodiment, a sample is mixed with a stream of a carrier solution to which an excess of titrant for neutralizing acids or bases in the sample has been added. The sample injected into the carrier solution is dispersed in the carrier solution to neutralize acids or bases in the sample with the titrant, but an excess of titrant has been added, so that a nonreacted titrant remains. In the above described manner, acids (or bases) in the sample have been neutralized and the carrier solution with the nonreacted titrant contained therein is joined with a stream of a pH buffer solution. The remaining process is the same as in the first embodiment so that its description is omitted.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved flow injection nonaqueous solvent neutralization titration process and apparatus.

Figure 1:
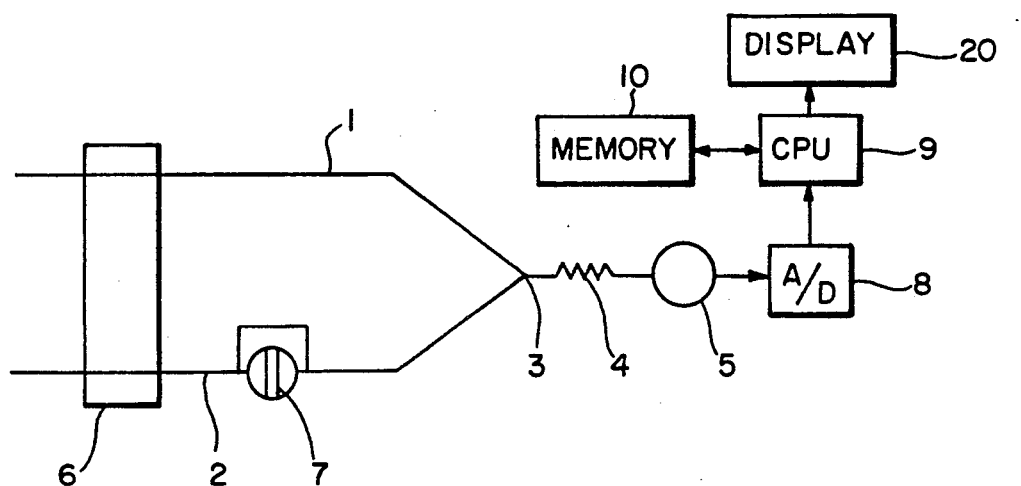
FIG. 1 is a schematic drawing showing a first preferred embodiment of the present invention.

A first preferred embodiment of a flow injection nonaqueous solvent neutralization titration according to the present invention is described for a titration apparatus shown by the schematic drawing of FIG. 1.

Referring to FIG. 1, reference numeral 1 designates a pH buffer solution line, and reference numeral 2 designates a carrier solution line. The pH buffer solution line 1 is connected with the carrier solution line 2 at a confluence point 3, a reaction coil 4 is arranged on the downstream side of the confluence point 3, and a pH-electrode detector 5 is arranged on the downstream side of the reaction coil 4. Reference numeral 6 designates a pump provided in the pH buffer solution line 1 and the carrier solution line 2 and reference numeral 7 designates an injector of a sample arranged in the carrier solution line 2.

A solution (pH=1.2) containing trichloro acetic acid/n-propyl amine of 10 mM and LiCl of 0.1 M is set in the pH buffer solution line 1 as a nonaqueous solvent pH buffer solution and a solvent comprising Toluene, isopropyl alcohol and water (50:49.5:0.5) is set in the carrier solution line 2 as a carrier solution. In addition, 4 ml of tri-n-propyl amine of 0 to 0.5 M is put into a beaker as a sample and a predetermined excess (50 ml) of HCl of 40 mM as a titrant is added in the beaker, which is sufficiently stirred to produce a mixture, whereby neutralizing the bases of the sample with the HCl. Thereupon, HCl is consumed in proportion to a base-number of the sample to leave a portion of a nonreacted HCl. This sample is set in the injector 7.

Then, the pumps 6 are driven to make the nonaqueous solvent pH buffer solution in the pH buffer solution line 1 and the carrier solution in the carrier solution line 2 flow, respectively, thereby injecting the sample in the injector 7 into the carrier solution within the carrier solution line 2. The resulting dispersion is joined with the nonaqueous solvent pH buffer solution in the pH buffer solution line 1 at the confluence point 3 and the remaining nonreacted HCl acts upon the ingredients of the nonaqueous solvent pH buffer solution at the reaction coil 4 to change a concentration ratio of acids to bases in the nonaqueous solvent pH buffer solution. This change of the concentration ratio of acids to bases is detected by means of a pH-electrode detector 5. When the sample is injected into the carrier solution line 2, the concentration ratio of acids to bases in the nonaqueous solvent pH buffer solution is changed, depending upon a quantity the remaining nonreacted HCl to change an output potential of the pH-electrode detector 5 to a positive side. This change of the output potential appears as a signal having a peak because the sample is dispersed in the carrier solution, so that a height of the peak is determined.

In addition, aniline of 0 to 0.5 M was used as the sample to determine the height of the peak of the output potential of the pH detector 5 in the above described manner.

Figure 2:
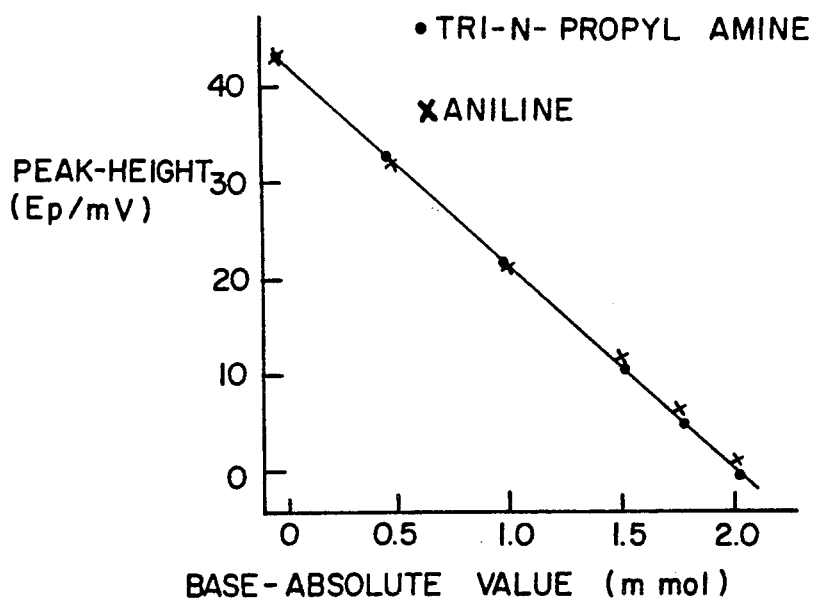
FIG. 2 is a calibration curve for a back titration.

The respective calibration curves in the back titrations of tri-n-propyl amine and aniline as the sample were as shown in FIG. 2. It is obvious from the calibration curves shown in FIG. 2 that the heights of the peaks of the respective signals for tri-n-propyl amine and aniline are linearly reduced with an increase of the base-number of the respective samples.

Figure 3:
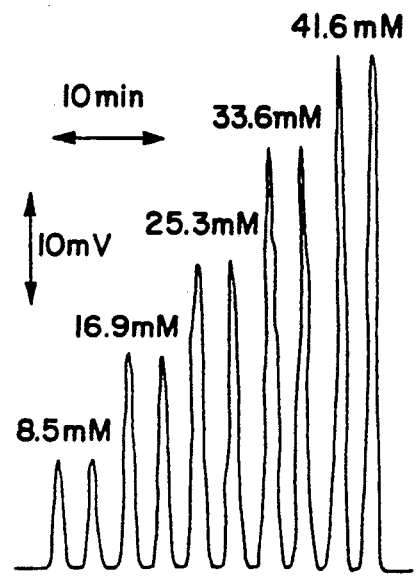
FIG. 3 is a calibration curve of a known substance.

8.5 to 41.6 mM of HCl as a known substance was set in the injector 7 to inject HCl into the carrier solution line 2 at regular intervals of 180 seconds, whereby determining the peak of the output potential of the pH detector 5 in the above described manner. And, the calibration curve formed from the heights of the peaks of the signal were as shown in FIG. 3 and a linear relation, passing a fundamental point, was found between the concentration of HCl and the height of the peak of the signal. In addition, a coefficient of variation of the heights of the peaks was 0.22% when HCl of 25.3 mM was injected 10 times.

The respective base-number of tri-n-propyl amine and aniline as the samples are measured from the peaks of the respective output signals shown in FIG. 2 on the basis of the calibration curve of the known substance HCl shown in FIG. 3.

In addition, it is possible also that an absorptivity detector is arranged in place of the pH detector 5, a pH indicator being added to the pH buffer solution, a change of absorptivity being detected by means of the absorptivity detector, and acids or bases of the sample being quantitatively determined from the heights of the peaks of the detected signal on the basis of the calibration curve of the known substance shown in FIG. 3.

As can be appreciated from FIG. 1, the output of the pH detector 5 can be digitized by an analogue to digital converter 8 and inputted into a CPU 9 through an appropriate 1/0 circuit (not shown). The calibration values that have been appropriately predetermined can be stored in a look-up table in a memory device 10. These values can be used to determine the actual concentration of the component in the sample that is to be detected and the concentration can then be displayed in display 20.

Figure 4:
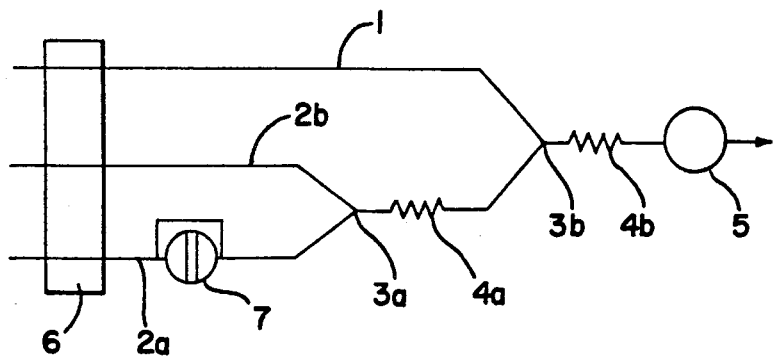
FIG. 4 is a schematic drawing showing a second preferred embodiment of the present invention.
Figure 5:
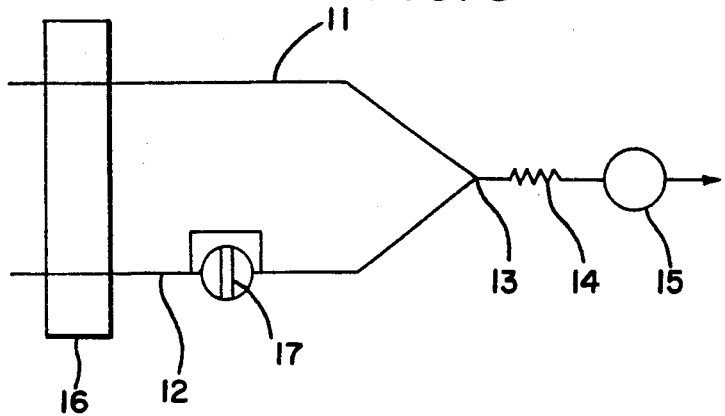
FIG. 5 is a schematic drawing of a conventional example.

A second preferred embodiment of a flow injection nonaqueous solvent neutralization titration process according to the present invention is described for a titration apparatus shown by FIG. 4.

Referring to FIG. 4, reference numeral 1 designates a pH buffer solution line, reference numeral 2a designates a first carrier solution line. The first carrier solution line 2a is connected with a second carrier solution line 2b at a confluence point 3a, a reaction coil 4a is arranged on the downstream side of the confluence point 3a. The reaction coil 4a is connected with the pH buffer solution line 1 at a confluence point 3b on the downstream side thereof, and a reaction coil 4b is arranged on the downstream side of the confluence point 3b. Reference numeral 5 designates a pH detector connected with the downstream side of the reaction coil 4b. Reference numeral 6 designates a pump provided in the pH buffer solution line 1, the first carrier solution line 2a and the second carrier solution line 2b. Reference numeral 7 designates an injector for a sample arranged in the first carrier solution line 2a.

In this titration apparatus, the sample is set in the injector 7 and a nonaqueous solvent pH buffer solution and a first carrier solution is set in the pH buffer solution line 1 and the first carrier solution line 2a, respectively. A second carrier solution, which is the same one as the first carrier solution, but containing a predetermined quantity of a titrant, such as HCl, which will be excessive to a neutralization of the sample is set in the second carrier solution, line 1b.

Subsequently, the pumps 6 are driven to make the nonaqueous pH buffer solution in the pH buffer solution line 1, the first carrier solution in the first carrier solution line 2a and the second carrier solution in the second carrier solution line 2b, respectively, flow and then the sample within the injector is injected into the first carrier solution within the first carrier solution line 2a to be diffused in the first carrier solution. The first carrier solution, in which the sample has been diffused, arrives at the confluence point 3a to be joined with the second carrier solution to which the excessive titrant within the second carrier solution line 2b has been added. As soon as the first carrier solution and the second carrier solution arrive at the reaction coil 4a, bases of the sample, diffused in the first carrier solution, are neutralized with the titrant added to the second carrier solution to consume the titrant in proportion to a base-number of the sample. However, an excess of titrant relatively to the base-number of the sample was purposely added, so that a portion of nonreacted titrant remains in the mixed first carrier solution and the second carrier solution.

The mixture of the first carrier solution and the second carrier solution, in which the titrant has been consumed in proportion to the base-number of the sample in the above described manner, are joined with the nonaqueous solvent pH buffer solution within the pH buffer solution line 1 at the confluence point 3b to further react the remaining nonreacted titrant upon ingredients of the nonaqueous solvent pH buffer solution, thereby changing a concentration ratio of acids to bases of the nonaqueous solvent pH buffer solution. A change of the concentration ratio of acids to bases is detected by means of the pH detector 5. An acid-number or base-number of the sample is measured from a height of a peak of the detected signal of the sample on the basis of a separately prepared calibration curve of a known substance.

As above described, in the flow injection nonaqueous solvent neutralization titration according to the present invention, a known quantity of an excess of titrant for neutralizing acids (or bases) in the sample are added to the sample and the resulting mixture is mixed with the carrier solution or the sample is mixed in the carrier solution to which an excess of titrant has been added. Thus, the sample is neutralized with the titrant, while leaving nonreacted titrant. As soon as the respective carrier solutions are joined with the pH buffer solution, the remaining titrant changes the concentration ratio of acids to bases of the pH buffer solution, so that this concentration ratio of acids to bases is detected by means of the detector. Acids (or bases) of the sample are quantitatively determined from the detected peak values on the basis of a separately prepared calibration curve, which was also derived from the same predetermined known quantity of titrant. A slope of the calibration curve is determined by a dissociation constant of the titrant.

Accordingly, it is possible also to easily and quantitatively determine acids (or bases) in a sample of which a dissociation constant is unknown. Moreover, acids (or bases) of the sample are quantitatively determined on the basis of the calibration curve of the known substance, so that it is unnecessary to strictly control a quantity and a concentration of the titrant, although the back titration, in which an excess of titrant is use, is introduced and it is possible to easily achieve the titration.

Furthermore, in a flow injection nonaqueous solvent neutralization titration process, the sample is mixed with the titrant to neutralize the former with the latter and then the resulting mixture is mixed with the carrier solution, so that also acids or bases of the sample, having a large viscosity, can be quantitatively determined with high accuracy.

The present invention adds an excess amount of a titration reagent that, in effect, exhausts the reaction components contained in the sample so that the sample is incapable of further reacting with the reagent. Subsequently, the mixture of the sample and the excessive reagent solution is introduced into a reaction cell to change the concentration of ratio of acids to bases of a pH buffer solution. This concentration ratio is then detected and, with the use of a separately prepared calibration curve, the acids or bases in the sample are determined.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of determining the concentration of a sample in a fluid carrier solution comprising the steps of:
   selecting a predetermined quantity of a known titrant;
   preparing calibration values based on the predetermined quantity of the known titrant for different predetermined concentrations of a desired component to be determined in the sample, the known titrant quantity being in excess of an amount necessary to completely react with the sample;
   adding the quantity of a known titrant to the sample and causing it to fully react with the sample;
   providing a fluid carrier solution for receiving the sample and titrant after they have interacted;
   inserting the sample and titrant by-products in the fluid carrier solution;
   providing a pH buffer solution;
   mixing the fluid carrier solution, with by-products of the reactions of the sample and titrant, in the pH buffer solution to change the concentration ratio of acids to bases by any active excess titrant;
   detecting any amount of an excess remaining titrant that has not reacted with the sample, and
   determining from the calibration values and the detected amount of excess titrant, the concentrations within the sample of the desired component.

2. The method of claim 1 wherein the pH buffer solution contains trichloro acetic acid/n-propyl amino and LiCl.

3. The method of claim 1 wherein the titrant is HCl.

4. The method of claim 1 wherein the change in concentration ratio is determined by a pH detector.

5. A method of determining the concentration of a sample in a fluid carrier solution comprising the steps of:
   selecting a predetermined quantity of a known titrant;
   preparing calibration values based on the predetermined quantity of the known titrant for different predetermined concentrations of a desired component to be determined in the sample, the known titrant quantity being in excess of an amount necessary to completely react with the sample;
   providing a fluid carrier solution for receiving the sample, the fluid carrier solution containing the quantity of the known titrant to react with the sample;
   providing a pH buffer solution;
   mixing the fluid carrier solution, with by-products of the reactions of the sample and titrant, in the pH buffer solution to change the concentration ratio of acids to bases by any active excess titrant;
   measuring the change in concentration ratio to detect the amount of excess titrant, and
   determining from the calibration values and the detected amount of excess titrant, the concentrations within the sample of the desired component.

6. The method of claim 5 wherein the pH buffer solution contains trichloro acetic acid/n-propyl amino and LiCl.

7. The method of claim 5 wherein the titrant is HCl.

* * * * *